US011691035B2

(12) United States Patent
Braida-Valerio et al.

(10) Patent No.: US 11,691,035 B2
(45) Date of Patent: Jul. 4, 2023

(54) OXIDIZING COMPOSITION FOR THE TREATMENT OF KERATIN FIBERS COMPRISING AT LEAST ONE CATIONIC POLYMER, AT LEAST ONE FATTY AMIDE AND AT LEAST ONE ANTI-OXYGEN AGENT

(75) Inventors: Damarys Braida-Valerio, Paris (FR); Laurent Nodari, St Leu (FR); Jean Cotteret, Maisons Laffite (FR)

(73) Assignee: L'OREAL, Paris (FR)

( * ) Notice: Subject to any disclaimer, the term of this patent is extended or adjusted under 35 U.S.C. 154(b) by 87 days.

(21) Appl. No.: 12/642,583

(22) Filed: Dec. 18, 2009

(65) Prior Publication Data

US 2010/0158839 A1  Jun. 24, 2010

Related U.S. Application Data

(60) Provisional application No. 61/144,217, filed on Jan. 13, 2009.

(30) Foreign Application Priority Data

Dec. 19, 2008 (FR) ...................................... 0858838

(51) Int. Cl.
| | |
|---|---|
| *A61K 8/30* | (2006.01) |
| *A61Q 5/08* | (2006.01) |
| *A61Q 5/12* | (2006.01) |
| *A61Q 5/10* | (2006.01) |
| *A61Q 5/04* | (2006.01) |
| *A61K 8/84* | (2006.01) |
| *A61K 8/22* | (2006.01) |
| *A61K 8/81* | (2006.01) |
| *A61K 8/45* | (2006.01) |
| *A61K 8/67* | (2006.01) |
| *A61K 8/46* | (2006.01) |

(52) U.S. Cl.
CPC .................. *A61Q 5/04* (2013.01); *A61K 8/22* (2013.01); *A61K 8/45* (2013.01); *A61K 8/466* (2013.01); *A61K 8/678* (2013.01); *A61K 8/817* (2013.01); *A61K 8/84* (2013.01); *A61Q 5/08* (2013.01); *A61Q 5/10* (2013.01); *A61K 2800/522* (2013.01); *A61K 2800/5426* (2013.01)

(58) Field of Classification Search
CPC ... A61Q 5/04; A61Q 5/10; A61Q 5/08; A61K 8/22; A61K 8/45; A61K 8/466; A61K 2800/522; A61K 2800/5426; A61K 8/817; A61K 8/84; A61K 8/678

See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,826,681 A | 5/1989 | Jacquet et al. | |
| 4,845,293 A | 7/1989 | Junino et al. | |
| 5,021,066 A | 6/1991 | Aeby et al. | |
| 5,259,849 A | 11/1993 | Grollier et al. | |
| 5,364,414 A | 11/1994 | Lang et al. | |
| 5,780,445 A * | 7/1998 | Schneider ............... | A61K 8/602 514/25 |
| 5,817,155 A | 10/1998 | Yasuda et al. | |
| 6,010,541 A | 1/2000 | De La Mettrie | |
| 6,074,439 A | 6/2000 | De La Mettrie et al. | |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |

(Continued)

FOREIGN PATENT DOCUMENTS

| | | |
|---|---|---|
| CA | 1 268 421 | 5/1990 |
| CA | 2 573 567 | 3/2006 |

(Continued)

OTHER PUBLICATIONS

LookChem, Poly[(dimethyliminio)-1,1,6-hexanediylchloride (1:2)], pp. 1-2, accessed Mar. 7, 2011.*
Lubrizol, Merquat 100 polymer, (accessed May 9, 2019), pp. 1-3 (Year: 2019).*
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.

(Continued)

*Primary Examiner* — Jianfeng Song
(74) *Attorney, Agent, or Firm* — The Marbury Law Group, PLLC

(57) ABSTRACT

Provided is a composition for the treatment of keratin fibers, for example human keratin fibers such as the hair, comprising, in a cosmetically acceptable medium, at least one cationic polymer; at least one fatty amide; at least one anti-oxygen agent; and at least one oxidizing agent; wherein the pH of the composition ranges from 1.5 to 4.5. Also provided is a composition for the treatment of keratin fibers, comprising, in a cosmetically acceptable medium, at least one cationic polymer; at least one fatty amide; at least one anti-oxygen agent; and at least one oxidizing agent; wherein the pH of the composition is alkaline. Also provided is a method for treating keratin fibers, comprising applying, to the keratin fibers, at least one oxidizing composition described herein.

16 Claims, No Drawings

(56) References Cited

U.S. PATENT DOCUMENTS

| | | |
|---|---|---|
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,294,152 B2 * | 11/2007 | Lagrange .......................... 8/405 |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,740,663 B2 | 6/2010 | De La Mettrie et al. |
| 7,766,977 B2 | 8/2010 | Cottard et al. |
| 7,799,095 B2 | 9/2010 | Mario et al. |
| 7,914,591 B2 | 3/2011 | Hercouet et al. |
| 7,922,777 B2 | 4/2011 | Hercouet et al. |
| 7,935,154 B2 | 5/2011 | Hercouet et al. |
| 7,981,165 B2 | 7/2011 | Simonet et al. |
| 7,988,737 B2 | 8/2011 | Hercouet et al. |
| 2002/0157193 A1 * | 10/2002 | Legrand .................. A61K 8/22 |
| | | 8/405 |
| 2002/0189034 A1 | 12/2002 | Kitabata et al. |
| 2003/0049281 A1 * | 3/2003 | Espinoza ................ A61K 8/14 |
| | | 424/400 |
| 2003/0064494 A1 * | 4/2003 | Kumar et al. ................ 435/189 |
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0172771 A1 | 9/2004 | Cottard et al. |
| 2004/0181883 A1 | 9/2004 | Legrand et al. |
| 2004/0221400 A1 * | 11/2004 | Cotteret et al. .................... 8/405 |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2005/0257331 A1 * | 11/2005 | Nocker et al. .................... 8/405 |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 * | 11/2006 | Kravtchenko et al. ........... 8/405 |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0116729 A1 * | 5/2007 | Palepu .......................... 424/400 |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |
| 2010/0162492 A1 | 7/2010 | Hercouet et al. |
| 2010/0175705 A1 | 7/2010 | Hercouet et al. |
| 2010/0178263 A1 | 7/2010 | Simonet et al. |
| 2010/0186177 A1 | 7/2010 | Hercouet et al. |
| 2010/0199441 A1 | 8/2010 | Hercouet et al. |

FOREIGN PATENT DOCUMENTS

| | | |
|---|---|---|
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 A1 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 198 42 071 | 3/2000 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 | 4/2009 |
| EP | 2 072 034 | 6/2009 |
| EP | 2 072 035 | 6/2009 |
| EP | 2 072 036 | 6/2009 |
| EP | 2 198 842 | 6/2010 |
| EP | 2 198 843 | 6/2010 |
| EP | 2 198 849 | 6/2010 |
| FR | 1 517 715 | 3/1968 |
| FR | 2 132 214 | 11/1972 |

(56) References Cited

FOREIGN PATENT DOCUMENTS

| | | |
|---|---|---|
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 A1 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| FR | 2 940 054 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 A | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 A2 | 7/2003 |
| WO | WO 03/084495 | 10/2003 |
| WO | WO 2005/025525 | 3/2005 |
| WO | WO 2005/055966 * | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 97/04739, dated Feb. 13, 1997.
European Search Report for EP 08 17 2444, dated Apr. 13, 2009.

(56) References Cited

OTHER PUBLICATIONS

European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance dated Aug. 10, 2010, in U.S. Appl. No. 12/339,820.
Notice of Allowance dated Aug. 26, 2010, in U.S. Appl. No. 12/642,624.
Notice of Allowance dated Aug. 26, 2010, in U.S. Appl. No. 12/642,637.
Notice of Allowance dated Aug. 27, 2010, in U.S. Appl. No. 12/642,513.
Notice of Allowance mailed in co-pending U.S. Appl. No. 12/339,753, dated Jul. 9, 2010.
Notice of Allowance dated Jun. 11, 2010, in U.S. Appl. No. 12/642,489.
Notice of Allowance dated Sep. 16, 2010, in U.S. Appl. No. 12/642,480.
Notice of Allowance dated Sep. 16, 2010, in U.S. Appl. No. 12/642,555.
Notice of Allowance dated Sep. 21, 2010, in U.S. Appl. No. 12/642,489.
Notice of Allowance dated Sep. 22, 2010, in U.S. Appl. No. 12/642,551.
Notice of Allowance dated Sep. 23, 2010, in U.S. Appl. No. 12/642,536.
Notice of Allowance dated Sep. 7, 2010, in U.S. Appl. No. 12/642,599.
Notice of Allowance dated Sep. 8, 2010, in U.S. Appl. No. 12/642,543.
Notice of Allowance dated Sep. 9, 2010, in U.S. Appl. No. 12/642,531.
Office Action dated Aug. 11, 2010, in co-pending U.S. Appl. No. 12/642,593.
Office Action dated Aug. 26, 2010, in co-pending U.S. Appl. No. 12/642,473.
Office Action dated Feb. 1, 2010, in co-pending U.S. Appl. No. 12/339,753.
Office Action dated Mar. 15, 2010, in co-pending U.S. Appl. No. 12/339,820.
Office Action dated Sep. 17, 2010, in co-pending U.S. Appl. No. 12/642,506.
Office Action dated Sep. 21, 2010, in co-pending U.S. Appl. No. 12/642,468.
Office Action dated Sep. 22, 2010, in co-pending U.S. Appl. No. 12/642,492.
Office Action dated Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
French Search Report for FR 0858838, dated Sep. 3, 2009.
English language abstract of DE 43 09 509 A1, Sep. 19, 1994.
English language abstract of DE 198 42 071, Mar. 16, 2000.
European Search Report for EP 10 15 5935, dated Oct. 8, 2010.
European Search Report for EP 10 19 5262, dated Apr. 1, 2011.
French Search Report for FR 09/59388, dated Aug. 3, 2010.
French Search Report for FR 09/59391, dated Sep. 16, 2010.
French Search Report for FR 09/59433, dated Sep. 24, 2010.
French Search Report for FR 09/59434, dated Sep. 24, 2010.
P.R. Canterbery et al., International Cosmetic Ingredient Dictionary and Handbook, vol. 1, p. 759 (2002).
STIC Search Report for U.S. Appl. No. 12/976,173, dated May 13, 2011.
Ullmann's Encyclopedia of Industrial Chemistry, "Hair Preparations," Wiley-VCH Verlag GnbH & Co., KGaA, Weinheim, p. 20 (2006).

* cited by examiner

OXIDIZING COMPOSITION FOR THE TREATMENT OF KERATIN FIBERS COMPRISING AT LEAST ONE CATIONIC POLYMER, AT LEAST ONE FATTY AMIDE AND AT LEAST ONE ANTI-OXYGEN AGENT

This application claims benefit of U.S. Provisional Application No. 61/144,217, filed Jan. 13, 2009. This application also claims benefit of priority under 35 U.S.C. § 119 to French Patent Application No. 0858838, filed Dec. 19, 2008.

Provided is a composition for the treatment of keratin fibers, for example human keratin fibers such as the hair, comprising, in a cosmetically acceptable medium, at least one cationic polymer; at least one fatty amide; at least one anti-oxygen agent; and at least one oxidizing agent.

In cosmetics, in the areas of dyeing, bleaching, and permanent deformation of keratin fibers, for example human keratin fibers such as the hair, oxidizing compositions are often used.

Thus, in oxidation dyeing of the hair, oxidizing compositions may be mixed with oxidation dyes (bases and couplers), which may be colorless in themselves, to produce colored and coloring compounds by a process of oxidative condensation. Oxidizing compositions may also be used in direct dyeing of the hair mixed with certain direct dyes which are colored and coloring, to obtain coloration with a hair-lightening effect. The oxidizing agents used conventionally for the dyeing of keratin fibers include for example hydrogen peroxide or compounds that can produce hydrogen peroxide by hydrolysis, such as urea peroxide. Persalts such as perborates and persulphates can also be used. Hydrogen peroxide for example can also be used.

In hair bleaching, the bleaching compositions may contain at least one oxidizing agent. Among these oxidizing agents, those conventionally used are for example hydrogen peroxide or compounds that can produce hydrogen peroxide by hydrolysis, such as urea peroxide or persalts such as perborates, percarbonates, and persulphates, hydrogen peroxide and persulphates being for example used.

These compositions can be aqueous compositions containing alkaline agents (amines or ammonia), which are diluted at the moment of use with an aqueous composition of hydrogen peroxide.

These compositions can also be formed from anhydrous products that contain alkaline compounds (amines and/or alkaline silicates), and a peroxidized reagent such as persulphates, perborates, or percarbonates, of ammonium or of alkali metals, which are diluted at the moment of use with an aqueous composition of hydrogen peroxide.

In permanent deformation of the hair, first the disulphide bonds —S—S— of the keratin (cystine) can be opened using a composition containing a suitable reducing agent (reduction stage) then, after rinsing the hair thus treated, secondly the disulphide bonds can be reconstituted by applying, on the hair previously put under tension (curlers etc.), an oxidizing composition (oxidation stage, also called fixation) so as finally to give the hair the desired form. This technique thus may make it possible to carry out either waving or straightening of the hair. The new shape imposed on the hair by chemical treatment as described above may be long-lasting and may withstand the action of washing with water or shampoos, in contrast to the conventional techniques of temporary waving, such as a water wave.

The oxidizing compositions used in the fixation stage are generally compositions based on hydrogen peroxide.

Moreover, in the cosmetic field, improved conditioning of the hair is desirable, i.e., for example improving the properties of smoothness and softness to the touch.

To do this, the use of cationic molecules is known, for example cationic polymers or cationic surfactants for improving fiber conditioning.

However, the inclusion of cationic polymers in oxidizing compositions based on hydrogen peroxide may lead to destabilization of these compositions.

Provided is a composition for the treatment of keratin fibers, for example human keratin fibers such as the hair, comprising, in a cosmetically acceptable medium:
  at least one cationic polymer;
  at least one fatty amide;
  at least one anti-oxygen agent; and
  at least one oxidizing agent.

Also provided is a composition for the treatment of keratin fibers comprising, in a cosmetically acceptable medium:
  at least one cationic polymer;
  at least one fatty amide;
  at least one anti-oxygen agent; and
  at least one oxidizing agent;
  wherein the pH of the composition ranges from 1.5 to 4.5.

Also provided is a composition for the treatment of keratin fibers comprising, in a cosmetically acceptable medium:
  at least one cationic polymer;
  at least one fatty amide;
  at least one anti-oxygen agent selected from vitamin E and the ethers and esters thereof; and
  at least one oxidizing agent;
  wherein the pH of the composition is alkaline.

When the composition described herein is used for coloring keratin fibers, good dyeing properties may be obtained, for example strong, chromatic coloring, low selectivity, and good resistance to the various aggressive factors to which the hair may be subjected, such as shampoos, light, sweat, and permanent deformation, without affecting the cosmetic properties of the keratin fibers.

When the composition described herein is used for the bleaching of keratin fibers, it may provide a good lightening effect of the fibers without degrading them and without affecting their cosmetic properties.

When the composition described herein is used for the permanent deformation of keratin fibers, it may provide satisfactory permanent deformation of the fibers without degrading them and without affecting their cosmetic properties.

Moreover, the composition described herein may have good stability over time, such as in storage at high temperatures, for example at a temperature of 45° C.

Also provided is a method for treating keratin fibers, such as a method for coloring, bleaching, or permanent deformation of keratin fibers, employing at least one oxidizing composition described herein.

Also provided is a method for making this oxidizing composition for treating keratin fibers.

Hereinafter, unless stated otherwise, the limits of the stated ranges are included.

"Cationic polymer" means any polymer containing cationic groups and/or groups ionizable to cationic groups.

Among the cationic polymers, non-limiting mention may be made for example of polyamine, polyaminoamide, and quaternary polyammonium polymers.

The polyamine, polyaminoamide, and quaternary polyammonium polymers which can be used in the composition described herein, are for example described in French patents FR 2 505 348 and FR 2 542 997. Among these polymers, non-limiting mention may be made of:

(1) the homopolymers or copolymers derived from esters or amides of acrylic or methacrylic acid;

(2) cationic cellulose derivatives such as:

(a) derivatives of cellulose ethers bearing quaternary ammonium groups described in French patent FR 1 492 597;

(b) copolymers of cellulose or cellulose derivatives grafted with a water-soluble quaternary ammonium monomer, for example those described in U.S. Pat. No. 4,131,576, such as hydroxyalkylcelluloses, for example hydroxymethyl, hydroxyethyl or hydroxypropyl celluloses for instance grafted with a salt of methacryloylethyl-trimethylammonium, of methacrylamidopropyl-trimethylammonium, or of dimethyldiallylammonium; polyquaternium 10 (INCI name) for example may be mentioned;

(3) other cationic polysaccharides described for example in U.S. Pat. Nos. 3,589,578 and 4,031,307, such as guar gums containing cationic trialkylammonium groups;

(4) polymers constituted of piperazinyl groups and linear or branched divalent alkylene or hydroxyalkylene groups, optionally interrupted by oxygen, sulphur, or nitrogen atoms or by aromatic or heterocyclic rings, as well as the products of oxidation and/or quaternization of these polymers. Such polymers are for example described in French patents FR 2 162 025 and FR 2 280 361;

(5) water-soluble polyaminoamides, such as those for example described in French patents FR 2 252 840 and FR 2 368 508;

(6) derivatives of polyaminoamides, for example adipic acid/dialkylaminohydroxyalkyldialkylene-triamine polymers in which the alkyl group has from 1 to 4 carbon atoms and for example represents a methyl, ethyl, or propyl group, and the alkylene group has from 1 to 4 carbon atoms, and for example represents the ethylene group. Such polymers are for instance described in French patent FR 1 583 363;

(7) the polymers obtained by reaction of a polyalkylene-polyamine bearing two primary amine groups and at least one secondary amine group, with a dicarboxylic acid selected from diglycolic acid and saturated aliphatic dicarboxylic acids having from 3 to 8 carbon atoms. The molar ratio of polyalkylene-polyamine to dicarboxylic acid may range from 0.8:1 to 1.4:1; the resultant polyaminoamide may be reacted with epichlorohydrin in a molar ratio of epichlorohydrin to the secondary amine group of the polyaminoamide ranging from 0.5:1 to 1.8:1. Such polymers are for example described in U.S. Pat. Nos. 3,227,615 and 2,961,347;

(8) cyclopolymers of alkyldiallylamine or of dialkyldiallylammonium such as the homopolymer of dimethyldiallylammonium chloride and copolymers of diallyldimethylammonium chloride and acrylamide;

(9) the quaternary diammonium polymers having a number-average molecular weight generally between 1,000 and 100,000, such as those described for example in French patents FR 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020; non-limiting mention may be made for example of hexadimethrine chloride (INCI name), marketed by the company CHIMEX under the reference MEXOMERE PO;

(10) quaternary polyammonium polymers such as those for example described in patent application EP-A-122 324;

(11) quaternary polymers of vinylpyrrolidone and vinylimidazole, for example the products marketed under the names Luviquat® FC 905, FC 550 and FC 370 by the company BASF;

(12) the polyamines such as Polyquart® H sold by HENKEL, referred to under the name "POLYETHYLENE GLYCOL (15) TALLOW POLYAMINE" in the CTFA dictionary;

(13) the crosslinked polymers of methacryloyloxyalkyl ($C_1$-$C_4$) trialkyl($C_1$-$C_4$)ammonium salts such as those marketed under the name SALCARE® SC 92, SALCARE® SC 95 and SALCARE® SC 96 by the Company ALLIED COLLOIDS; and mixtures thereof.

Other cationic polymers that can be used are cationic proteins or hydrolysates of cationic proteins, polyalkylene imines, for example polyethylene imines, polymers containing vinylpyridine or vinylpyridinium units, condensates of polyamines and epichlorohydrin, quaternary polyureylenes, and chitin derivatives.

The at least one cationic polymer may for example be selected from the polymers as defined in points (8) and (9), and for example hexadimethrine chloride and the homo- or copolymers of dimethyldiallylammonium chloride. For instance, the at least cationic polymer may be selected from hexadimethrine chloride and polydimethyldiallylammonium chloride.

In some embodiments, the composition described herein comprises at least two cationic polymers.

In some embodiments, the at least one cationic polymer may have a cationic charge density greater than 3 meq./g, for example ranging from 3.5 to 8.5 meq./g. The charge density can be determined experimentally by Kjeldahl's method or by calculation from the structure of the polymer.

The at least one cationic polymer may be present in an amount ranging from 0.01 to 20% by weight, such as from 0.1 to 10% by weight, relative to the total weight of the composition.

"Fatty amide" means, as used herein, an amide that includes in its structure a hydrocarbon chain having at least 6 carbon atoms.

In some embodiments, the at least one fatty amide is selected from those of formula (I):

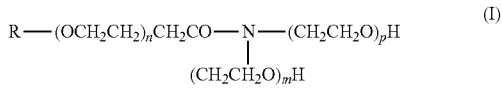

(I)

wherein:

R is a saturated or unsaturated, linear or branched $C_8$-$C_{30}$ alkyl radical, optionally substituted with at least one radical selected from an $OR_5$ radical, an $NR_6R_7$ radical, a carboxyl radical, a sulphonic radical, a carboxamido radical $CONR_6R_7$, a sulphonamido radical $SO_2NR_6R_7$, a heteroaryl, and an aryl radical optionally substituted with at least one entity selected from ($C_1$-$C_4$)alkyl, hydroxy, $C_1$-$C_2$ alkoxy, amino, and (di)alkyl($C_1$-$C_2$)amino groups;

$R_5$, $R_6$, and $R_7$, which may be identical or different, represent:

a hydrogen atom;

a linear or branched $C_1$-$C_4$ alkyl radical optionally substituted with at least one radical selected from a hydroxyl, a $C_1$-$C_2$ alkoxy, a carboxamido $CONR_8R_9$, a sulphonyl $SO_2R_8$, and an aryl radical optionally substituted with a ($C_1$-$C_4$)alkyl, hydroxy, $C_1$-$C_2$ alkoxy, amino, or (di)alkyl ($C_1$-$C_2$)amino radical; or an aryl radical optionally substituted with a $(C_1-C_4)$alkyl, hydroxy, $C_1-C_2$ alkoxy, amino, or (di)alkyl$(C_1-C_2)$amino radical;

$R_6$ and $R_7$, which may be identical or different, can also represent a carboxamido radical $CONR_8R_9$ or a sulphonyl radical $SO_2R_8$;

$R_8$ and $R_9$, which may be identical or different, represent a hydrogen atom or a linear or branched $C_1-C_4$ alkyl radical optionally substituted with at least one hydroxyl or $C_1-C_2$ alkoxy radical; and n, m, and p, which may be identical or different, are integers ranging from 0 to 10, wherein m+p≥1.

In some embodiments, R is a $C_{10}-C_{18}$ alkyl group.

In some embodiments, n is an integer ranging from 0 to 5.

In some embodiments, m is an integer ranging from 0 to 1.

In some embodiments, p is an integer ranging from 1 to 5.

As examples of the at least one fatty amide selected from those of formula (I), non-limiting mention may be made of the ethoxylated amides of colza acids such as the product referenced under the INCI name PEG-4 RAPESEED AMIDE.

In some embodiments, n is 0.

The at least one fatty amide may be present in an amount ranging from 0.1 to 20% by weight, for example from 0.2 to 10% by weight, such as from 0.5 to 5% by weight, relative to the total weight of the composition.

"Anti-oxygen agent" means, as used herein, an agent that can interact chemically with oxygen. Kinetically, this chemical interaction may be very fast. The at least one anti-oxygen agent present in the composition described herein may be selected from the antioxidants used conventionally in cosmetics, such as in the field of hair care.

In some embodiments, the at least one anti-oxygen agent may be selected from vitamin E and the derivatives thereof, erythorbic acid, ascorbic acid, hydroquinone, and the derivatives thereof such as alkylhydroquinones. In some embodiments, the derivatives of vitamin E may be selected from the ethers and esters of vitamin E.

In some embodiments, the at least one anti-oxygen agent may be selected from vitamin E and the derivatives thereof. In some embodiments, Vitamin E is used.

In some embodiments, the at least one oxidizing agent can be selected from hydrogen peroxide, persalts such as persulphates, percarbonates, and perborates, urea peroxide, alkaline bromates, and polythionates. In some embodiments, hydrogen peroxide is used.

In some embodiments, the at least one oxidizing agent may be present in an amount ranging from 0.1 to 50% by weight, such as from 1 to 20% by weight, relative to the total weight of the composition.

In some embodiments, when the at least one oxidizing agent is hydrogen peroxide, the composition described herein may comprise at least one agent that stabilizes hydrogen peroxide.

As examples of agents that stabilize hydrogen peroxide, non-limiting mention may be made of the pyrophosphates of the alkali or alkaline-earth metals such as tetrasodium pyrophosphate, the stannates of the alkali or alkaline-earth metals, and phenacetin or the salts of acids and of oxyquinoline, such as oxyquinoline sulphate. In some embodiments, at least one stannate may be used, optionally combined with at least one pyrophosphate.

In some embodiments, the at least one agent that stabilizes hydrogen peroxide may be present in an amount ranging from 0.0001 to 5% by weight, such as from 0.01 to 2% by weight, relative to the total weight of the composition.

In some embodiments, the composition further comprises at least one oil, which can be selected from non-siliconized mineral, vegetable, animal, or synthetic oil, and a silicone oil. In some embodiments, the composition may comprise at least one oil selected from non-siliconized mineral, vegetable, animal, and synthetic oils.

"Oil" means, as used herein, a substance that is liquid at 25° C. and at atmospheric pressure (760 mm of mercury), insoluble at those conditions in water at a concentration of 5%, and for example at a concentration of 1%, and has at least two siloxane groups or at least one hydrocarbon chain with at least 6 carbon atoms.

As non-siliconized oils which may be used in the composition described herein, non-limiting mention may be made, for example, of:

hydrocarbon oils of animal origin, such as perhydrosqualene;

hydrocarbon oils of vegetable origin, such as liquid triglycerides of fatty acids having from 6 to 30 carbon atoms such as triglycerides of heptanoic or octanoic acids or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, and shea butter oil;

linear or branched hydrocarbons containing at least 6 carbon atoms, of mineral or synthetic origin, such as $C_6-C_{16}$ lower alkanes such as hexane, dodecane, isododecane and isohexadecane, hydrocarbons with more than 16 carbon atoms such as paraffin oils, and the derivatives thereof, vaseline, vaseline oil, polydecenes, and hydrogenated polyisobutene such as PARLEAM®;

fluorinated, partially hydrocarbon oils; as fluorinated oils, non-limiting mention may also be made of perfluoromethylcyclopentane and perfluoro-1,3-dimethylcyclohexane, sold under the names "FLUTEC® PC1" and "FLUTEC® PC3" by the Company BNFL Fluorochemicals; perfluoro-1,2-dimethylcyclobutane; perfluoroalkanes such as dodecafluoropentane and tetradecafluorohexane, sold under the names "PF 5050" and "PE 5060®" by the 3M Company, or bromoperfluorooctyl sold under the name "FORALKYL®" by the company Atochem; nonafluoromethoxybutane and nonafluoroethoxyisobutane; and derivatives of perfluoromorpholine, such as 4-trifluoromethyl perfluoromorpholine sold under the name "PF 5052®" by the 3M Company;

the liquid $C_7-C_{30}$ fatty alcohols, and for example the unsaturated and/or branched $C_{10}-C_{22}$ fatty alcohols such as oleic alcohol or isostearyl alcohol, the liquid esters of acids and/or of fatty alcohol other than the triglycerides, and for example those for which the acid and/or the alcohol is/are unsaturated or branched, and for instance isopropyl myristate can be used.

The silicone oils can be selected from the cyclic polydialkylsiloxanes having from 3 to 7 silicon atoms, such as from 4 to 5 silicon atoms. They can be, for example, octamethylcyclotetrasiloxane marketed for example under the name VOLATILE SILICONE® 7207 by UNION CARBIDE or SILBIONE® 70045 V2 marketed by RHODIA, decamethylcyclopentasiloxane marketed under the name VOLATILE SILICONE® 7158 by UNION CARBIDE, and SILBIONE® 70045 V5 marketed by RHODIA, and mixtures thereof.

Non-limiting mention may also be made of the cyclocopolymers of the dimethylsiloxanes/methylalkylsiloxane type, such as SILICONE VOLATILE® FZ 3109 marketed by the company UNION CARBIDE, of formula:

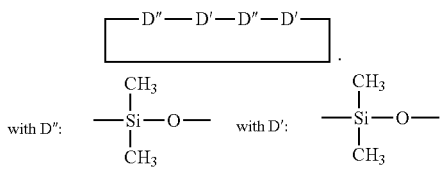

Non-limiting mention may also be made of the mixtures of cyclic polydialkylsiloxanes with organic compounds derived from silicon, such as the mixture of octamethylcyclotetrasiloxane and tetratrimethylsilylpentaerythritol (50/50), and the mixture of octamethylcyclotetrasiloxane and oxy-1,1'-(hexa-2,2,2',2',3,3'-trimethylsilyloxy) bis-neopentane;

the volatile linear polydialkylsiloxanes with 2 to 9 silicon atoms and having a viscosity less than or equal to $5.10^{-6}$ m$^2$/s at 25° C.; for example, decamethyltetrasiloxane marketed for example under the name "SH 200" by the company TORAY SILICONE. Silicones falling within this class are also described for instance in the article published in Cosmetics and Toiletries, Vol. 91, January 76, p. 27-32-TODD & BYERS "Volatile Silicone fluids for cosmetics."

Non-volatile polydialkylsiloxanes, gums and resins of polydialkylsiloxanes, polyorganosiloxanes modified with the aforementioned organofunctional groups, and mixtures thereof may for example be used.

These silicones may for example be selected from the polydialkylsiloxanes, among which non-limiting mention may be made of the polydimethylsiloxanes with trimethylsilyl end groups. The viscosity of the silicones is measured at 25° C. according to standard ASTM 445 Appendix C.

Among these polydialkylsiloxanes, the following non-limiting commercial products may be mentioned:

the SILBIONE® oils of series 47 and 70 047 or the MIRASIL® oils marketed by RHODIA such as, for example, the oil 70 047 V 500 000;

the oils of the MIRASIL® series marketed by the company RHODIA;

the oils of the 200 series from the company DOW CORNING such as DC200, with a viscosity of 60 000 mm$^2$/s;

the VISCASIL® oils from GENERAL ELECTRIC and certain oils of the SF series (SF 96, SF 18) from GENERAL ELECTRIC.

In some embodiments, the at least one oil may be present in an amount ranging from 0 to 60% by weight, for example from 10 to 60% by weight, such as from 15 to 55% by weight, such as from 20 to 50% by weight, relative to the total weight of the composition.

In some embodiments, the composition described herein comprises at least one oil different from fatty alcohols, which may be present in an amount of at least 10% by weight, for example at least 15% by weight, such as at least 20% by weight, relative to the total weight of the composition.

In some embodiments, the composition described herein comprises neither dye nor persalt.

"Cosmetically acceptable medium" means, as used herein, a medium compatible with keratin fibers, for example human keratin fibers such as the hair.

In some embodiments, the cosmetically acceptable medium of the composition described herein generally comprises water and/or at least one water-soluble organic solvent. As examples of water-soluble organic solvents, non-limiting mention may be made for example of the $C_1$-$C_4$ lower alkanols, such as ethanol and isopropanol; aromatic alcohols such as benzyl alcohol or phenoxyethanol; polyols or polyol ethers such as the monomethyl, monoethyl and monobutyl ethers of ethylene glycol, propylene glycol or ethers thereof such as monomethyl ether of propylene glycol, butylene glycol, dipropylene glycol as well as alkyl ethers of diethylene glycol such as monoethyl ether or monobutyl ether of diethylene glycol, or glycerol; and mixtures thereof.

In some embodiments, the solvents may for example be present in an amount ranging from 0.1 to 35% by weight, relative to the total weight of the composition described herein, such as from 1 to 40% by weight.

In some embodiments, the composition can also comprise additional compounds used conventionally in cosmetics. These compounds can for example be selected from thickening or stabilizing polymers, non-silicone conditioner polymers, silicones, chelating agents, and perfumes.

Of course, a person skilled in the art will take care to select this or these optional supplementary compound(s) in such a way that the beneficial properties associated with the composition described herein are not, or substantially are not, affected by the addition or additions envisaged.

The composition can be in various forms, such as in the form of cream, gel, milk, lotion, or mousse, or in any other suitable form for carrying out the treatment of keratin fibers, for example human keratin fibers such as the hair. For example, it can be in the form of a cream or a milk.

In some embodiments, the pH of the composition may range from 1.5 to 4.5, for example from 2 to 3.5. It can be adjusted by adding acidifying agents such as hydrochloric acid, acetic acid, lactic acid, boric acid, citric acid and phosphoric acid or acidifying agents in the presence of alkaline agents.

Also provided is a method for treating keratin fibers, comprising applying to the keratin fibers at least one oxidizing composition comprising, in a cosmetically acceptable medium:
  at least one cationic polymer;
  at least one fatty amide;
  at least one anti-oxygen agent; and
  at least one oxidizing agent;
  wherein the pH of the composition ranges from 1.5 to 4.5.

Also provided is a method for treating keratin fibers, comprising applying to the keratin fibers at least one oxidizing composition comprising, in a cosmetically acceptable medium:
  at least one cationic polymer;
  at least one fatty amide;
  at least one anti-oxygen agent selected from vitamin E and the ethers and esters thereof; and
  at least one oxidizing agent;
  wherein the pH of the composition is alkaline.

The at least one oxidizing composition described herein can for example be used in a method of dyeing keratin fibers, for example human keratin fibers such as the hair.

The method of dyeing of keratin fibers described herein may employ at least one dyeing composition comprising, in a support suitable for dyeing keratin fibers, at least one direct dye and/or at least one oxidation dye and at least one oxidizing composition.

This method comprises applying the at least one dyeing composition to the keratin fibers and developing the color at acidic, neutral, or alkaline pH by means of at least one oxidizing composition, which is applied simultaneously or sequentially, with or without intermediate rinsing.

In some embodiments, the at least one dyeing composition may be mixed, at the moment of use, with the at least one oxidizing composition described herein. The mixture obtained may then be applied to the keratin fibers and left in place for a period of time ranging from 3 to 50 minutes, such as from 5 to 30 minutes, followed by rinsing, washing with shampoo, rinsing again, and drying.

The at least one direct dye can be selected from the direct dyes used conventionally in direct dyeing. As non-limiting examples, the at least one direct dye may be selected from the nitro dyes of the benzene series, the azo direct dyes, methine direct dyes, quinone direct dyes, azine direct dyes, triarylmethane direct dyes, indoamine direct dyes, and natural direct dyes. These direct dyes can be of nonionic, anionic, or cationic character.

Among the benzene direct dyes, non-limiting mention may be made of 1,4-diamino-2-nitrobenzene, 1-amino-2-nitro-4-(β-hydroxyethylamino)-benzene, 1-amino-2-nitro-4-bis-(β-hydroxyethyl)-aminobenzene, 1,4-bis-(β-hydroxyethylamino)-2-nitrobenzene, 1-β-hydroxyethylamino-2-nitro-4-bis-(β-hydroxyethylamino)-benzene, 1-β-hydroxyethylamino-2-nitro-4-aminobenzene, 1-β-hydroxyethylamino-2-nitro-4-(ethyl)(β-hydroxyethylyaminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis-(β-hydroxyethylamino)-4-nitrobenzene, 1-amino-2-[tris-(hydroxymethyl)-methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropylamino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis-(β-hydroxyethyl)-amino]-3-nitrobenzene, 1-β-hydroxyethylamino-2-nitrobenzene, and 1-hydroxy-4-β-hydroxyethylamino-3-nitrobenzene.

Among the azo direct dyes, non-limiting mention may be made of the cationic azo dyes described in patent applications WO 95/15144, WO 95/01772, EP 0 714 954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Among these dyes, non-limiting mention may be made of for example 1,3-dimethyl-2-[[4-(dimethylamino)phenyl]azo]-1H-imidazolium chloride, 1,3-dimethyl-2-[(4-aminophenyl)azo]-1H-imidazolium chloride, and 1-methyl-4-[(methylphenylhydrazono)methyl]-pyridinium methylsulphate.

Non-limiting mention may also be made of, among the azo direct dyes, the following dyes described in the COLOUR INDEX INTERNATIONAL 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, and Disperse Black 9.

Non-limiting mention may also be made of 1-(4'-aminodiphenylazo)-2-methyl-4-bis-β3-hydroxyethyl)aminobenzene and 4-hydroxy-3-(2-methoxyphenylazo)-1-naphthalene sulphonic acid.

Among the quinone direct dyes, non-limiting mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, and Basic Blue 99, as well as the following dyes: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, and 1,4-bis-(β,γ-dihydroxypropylamino)-anthraquinone.

Among the azine dyes, non-limiting mention may be made of the following dyes: Basic Blue 17 and Basic Red 2.

Among the triarylmethane dyes, non-limiting mention may be made of the following dyes: Basic Green 1, Acid Blue 9, Basic Violet 3, Basic Violet 14, Basic Blue 7, Acid Violet 49, Basic Blue 26, and Acid Blue 7.

Among the indoamine dyes, non-limiting mention may be made of the following dyes: 2-β-hydroxyethlyamino-5-[bis-(β-4'-hydroxyethyl)amino]anilino-1,4-benzoquinone, 2-β-hydroxyethylamino-5-(2'-methoxy-4'-amino)anilino-1,4-benzoquinone, 3-N(2'-chloro-4'-hydroxy)phenyl-acetylamino-6-methoxy-1,4-benzoquinone imine, 3-N(3'-chloro-4'-methylamino)phenyl-ureido-6-methyl-1,4-benzoquinone imine, and 3-[4'-N-(ethyl, carbamylmethyl)-amino]-phenyl-ureido-6-methyl-1,4-benzoquinone imine.

Among the natural direct dyes that can be used, non-limiting mention may be made of lawsone, juglone, alizarin, purpurin, carminic acid, kermesic acid, purpurogallin, protocatechaldehyde, indigo, isatin, curcumin, spinulosin, apigenidin, and orceins. It is also possible to use extracts or decoctions containing these natural dyes, such as cataplasms or extracts based on henna.

The at least one direct dye may generally be present in the dyeing composition in an amount ranging from 0.001 to 20% by weight, relative to the total weight of the composition, such as from 0.005 to 10% by weight.

The at least one oxidation dye can be selected from the oxidation bases and couplers conventionally used in the area of dyeing.

As examples of oxidation bases, non-limiting mention may be made of para-phenylenediamines, double bases, para-aminophenols, ortho-aminophenols, and heterocyclic bases and the addition salts thereof.

Among the para-phenylenediamines, non-limiting mention may be made of, for example, para-phenylenediamine, para-toluenediamine, 2-chloro-para-phenylenediamine, 2,3-dimethyl para-phenylenediamine, 2,6-dimethyl para-phenylenediamine, 2,6-diethyl para-phenylenediamine, 2,5-dimethyl para-phenylenediamine, N,N-dimethyl para-phenylenediamine, N,N-diethyl para-phenylenediamine, N,N-dipropyl para-phenylenediamine, 4-amino N,N-diethyl 3-methyl aniline, N,N-bis-(β-hydroxyethyl) para-phenylenediamine, 4-N,N-bis-(β-hydroxyethyl)amino-2-methyl aniline, 4-N,N-bis-(β-hydroxyethyl)amino-2-chloro aniline, 2-β-hydroxyethyl para-phenylenediamine, 2-fluoro para-phenylenediamine, 2-isopropyl para-phenylenediamine, N-(β-hydroxypropyl) para-phenylenediamine, 2-hydroxymethyl para-phenylenediamine, N,N-dimethyl 3-methyl para-phenylenediamine, N,N-(ethyl, β-hydroxyethyl) para-phenylenediamine, N-(β,γ-dihydroxypropyl) para-phenylenediamine, N-(4'-aminophenyl) para-phenylenediamine, N-phenyl para-phenylenediamine, 2-β-hydroxyethyloxy para-phenylenediamine, 2-β-acetylaminoethyloxy para-phenylenediamine, N-(β-methoxyethyl) para-phenylene-diamine, 4-aminophenylpyrrolidine, 2-thienyl para-phenylenediamine, 2-βhydroxyethylamino-5-aminotoluene, 3-hydroxy 1-(4'-aminophenyl)pyrrolidine, and the addition salts thereof with an acid.

Among the para-phenylenediamines mentioned herein, para-phenylenediamine, para-toluenediamine, 2-isopropyl para-phenylenediamine, 2-β-hydroxyethyl para-phenylenediamine, 2-β-hydroxyethyloxy para-phenylene-diamine, 2,6-dimethyl para-phenylenediamine, 2,6-diethyl para-phenylenediamine, 2,3-dimethyl para-phenylenediamine, N,N-bis-(β-hydroxyethyl) para-phenylenediamine, 2-chloro para-phenylenediamine, 2-β-acetylaminoethyloxy para-phenylenediamine, and the addition salts thereof with an acid may for example be used.

Among the double bases, non-limiting mention may be made of, as examples, bis-phenylalkylenediamines and bis-para-aminophenols.

Among the bis-phenylalkylenediamines, non-limiting mention may be made of, as examples, N,N'-bis-(β-hydroxyethyl) N,N'-bis-(4'-aminophenyl) 1,3-diamino propanol, N,N'-bis-(β-hydroxyethyl) N,N'-bis-(4'-aminophenyl) ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methylphenyl) ethylenediamine, 1,8-bis-(2,5-diamino phenoxy)-3,6-dioxaoctane, and the addition salts thereof with an acid.

Among the para-aminophenols, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl aminomethyl)phenol, 4-amino-2-fluorophenol, and the addition salts thereof with an acid.

Among the ortho-aminophenols, non-limiting mention may be made of, for example, 2-aminophenol, 2-amino-5-methylphenol, 2-amino-6-methylphenol, 5-acetamido-2-aminophenol, and the addition salts thereof with an acid.

Among the heterocyclic bases, non-limiting mention may be made of, for example, pyridine derivatives, pyrimidine derivatives, and pyrazole derivatives.

Among the pyridine derivatives, non-limiting mention may be made of the derivatives described for example in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the addition salts thereof with an acid.

Other pyridine oxidation bases that can for example be used are the oxidation bases 3-aminopyrazolo-[1,5-a]-pyridines and the addition salts thereof, described for example in patent application FR 2 801 308. As examples, non-limiting mention may be made of pyrazolo[1,5-a]pyridin-3-ylamine, 2-acetylaminopyrazolo-[1,5-a]pyridin-3-ylamine; 2-morpholin-4-yl-pyrazolo[1,5-a]pyridin-3-ylamine; 3-amino-pyrazolo[1,5-a]pyridine-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridin-5-ol; 3-amino-pyrazolo[1,5-a]pyridin-4-ol; and 3-amino-pyrazolo[1,5-a]pyridin-6-ol; 3-amino-pyrazolo[1,5-a]pyridin-7-ol; as well as the addition salts thereof with an acid or with a base.

Among the pyrimidine derivatives, non-limiting mention may be made of the derivatives described for example in patents DE 2359399; JP 88-169571; JP 05-63124; EP 0770375 and patent application WO 96/15765, such as 2,4,5,6-tetra-aminopyrimidine, 4-hydroxy 2,5,6-triaminopyrimidine, 2-hydroxy 4,5,6-triaminopyrimidine, 2,4-dihydroxy 5,6-diaminopyrimidine, and 2,5,6-triaminopyrimidine; and pyrazolo-pyrimidine derivatives such as those mentioned in patent application FR-A-2750048 and among which non-limiting mention may be made of pyrazolo-[1,5-a]-pyrimidine-3,7-diamine; 2,5-dimethyl pyrazolo-[1,5-a]-pyrimidine-3,7-diamine, pyrazolo-[1,5-a]-pyrimidine-3,5-diamine; 2,7-dimethylpyrazolo-[1,5-a]-pyrimidine-3,5-diamine; 3-aminopyrazolo-[1,5-a]-pyrimidin-7-ol; 3-aminopyrazolo-[1,5-a]-pyrimidin-5-ol; 2-(3-aminopyrazolo-[1,5-a]-pyrimidin-7-ylamino)-ethanol, 2-(7-aminopyrazolo-[1,5-a]-pyrimidin-3-ylamino)-ethanol, 2-[(3-aminopyrazolo[1,5-a]pyrimidin-7-yl)-(2-hydroxy-ethyl)-amino]-ethanol, 2-[(7-amino-pyrazolo[1,5-a]pyrimidin-3-yl)-(2-hydroxy-ethyl)-amino]-ethanol, 5,6-dimethylpyrazolo-[1,5-a]-pyrimidine-3,7-diamine, 2,6-dimethylpyrazolo-[1,5-a]-pyrimidine-3,7-diamine, 2,5, N 7, N 7-tetramethyl pyrazolo-[1,5-a]-pyrimidine-3,7-diamine, 3-amino-5-methyl-7-imidazolylpropylaminopyrazolo-[1,5-a]-pyrimidine and the addition salts thereof with an acid and the tautomeric forms thereof, when there is tautomeric equilibrium.

Among the pyrazole derivatives, non-limiting mention may be made of the derivatives described in patents DE 3843892 and DE 4133957 and patent applications WO 94/08969, WO 94/08970, FR-A-2 733 749, and DE 195 43 988, such as 4,5-diamino 1-methylpyrazole, 4,5-diamino 1-(p-hydroxyethyl)pyrazole, 3,4-diaminopyrazole, 4,5-diamino 1-(4'-chlorobenzyl)pyrazole, 4,5-diamino 1,3-dimethylpyrazole, 4,5-diamino-3-methyl 1-phenyl pyrazole, 4,5-diamino 1-methyl 3-phenyl pyrazole, 4-amino 1,3-dimethyl 5-hydrazino pyrazole, 1-benzyl 4,5-diamino-3-methylpyrazole, 4,5-diamino-3-tert-butyl 1-methylpyrazole, 4,5-diamino 1-tert-butyl 3-methylpyrazole, 4,5-diamino 1-(β-hydroxyethyl) 3-methylpyrazole, 4,5-diamino 1-ethyl 3-methylpyrazole, 4,5-diamino 1-ethyl 3-(4'-methoxyphenyl)pyrazole, 4,5-diamino 1-ethyl 3-hydroxymethylpyrazole, 4,5-diamino-3-hydroxymethyl 1-methylpyrazole, 4,5-diamino-3-hydroxymethyl 1-isopropyl pyrazole, 4,5-diamino-3-methyl 1-isopropyl pyrazole, 4-amino-5-(2'-aminoethyl)amino 1,3-dimethyl pyrazole, 3,4,5-triaminopyrazole, 1-methyl 3,4,5-triaminopyrazole, 3,5-diamino 1-methyl 4-methylaminopyrazole, 3,5-diamino 4-(β-hydroxyethyl)amino 1-methylpyrazole, and the addition salts thereof with an acid.

As pyrazole derivatives, non-limiting mention may also be made of the diamino-N,N-dihydropyrazopyrazolones and for example those described in application FR 2 886 136 such as the following derivatives and the addition salts thereof.

Among these derivatives, non-limiting mention may be made of the following:
2,3-diamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one,
4,5-diamino-1,2-dimethyl-1,2-dihydro-pyrazol-3-one,
4,5-diamino-1,2-diethyl-1,2-dihydro-pyrazol-3-one,
4,5-diamino-1,2-di-(2-hydroxyethyl)-1,2-dihydro-pyrazol-3-one,
2-amino-3-(2-hydroxyethyl)amino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one,
2,3-diamino-5,6,7,8-tetrahydro-1H,6H-pyridazino[1,2-a]pyrazol-1-one,
4-amino-1,2-diethyl-5-(pyrrolidin-1-yl)-1,2-dihydro-pyrazol-3-one,
4-amino-5-(3-dimethylamino-pyrrolidin-1-yl)-1,2-diethyl-1,2-dihydro-pyrazol-3-one, and
2,3-diamino-6-hydroxy-6,7-dihydro-1H,5H-pyrazolo[1,2-a]pyrazol-1-one.

For example, 4,5-diamino 1-(β-hydroxyethyl)pyrazole, 2,3-diamino-6,7-dihydro-1H,5H-pyrazolo[1,2-a]pyrazol-1-one and the addition salts thereof may be used as heterocyclic bases.

In some embodiments, the at least one oxidation base may generally be present in the dyeing composition in an amount ranging from 0.001 to 10% by weight, relative to the total weight of the composition, such as from 0.005 to 6% by weight.

As examples of couplers, non-limiting mention may be made of meta-phenylenediamines, meta-aminophenols, meta-diphenols, naphthalenic couplers, heterocyclic couplers, and the addition salts thereof.

Non-limiting mention may also be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy 2-methyl benzene, 4-chloro 1,3-dihydroxybenzene, 2,4-diamino 1-(β-hydroxyethyloxy) benzene, 2-amino 4-(β-hydroxyethylamino) 1-methoxybenzene, 1,3-diamino benzene, 1,3-bis-(2,4-diaminophenoxy) propane, 3-ureido aniline, 3-ureido 1-dimethylamino benzene, sesamol, 1-(β-hydroxyethylamino-3,4-methylenedioxybenzene, α-naphthol, 2-methyl-1-naphthol, 6-hydroxy indole, 4-hydroxy indole, 4-hydroxy N-methyl indole, 2-amino-3-hydroxypyridine, 6-hydroxy benzomorpholine 3,5-diamino-2,6-dimethoxypyridine, 1-N-(β-hydroxyethyl) amino-3,4-methylene dioxybenzene, 2,6-bis-(β-hydroxyethylamino)toluene, and the addition salts thereof with an acid.

In some embodiments, the at least one coupler may generally be present in the dyeing composition in an amount ranging from 0.001 to 10% by weight, relative to the total weight of the composition, such as from 0.005 to 6% by weight.

In general, the addition salts of the at least one oxidation base and of the at least one coupler that can be used are for example selected from the addition salts thereof with an acid, such as hydrochlorides, hydrobromides, sulphates, citrates, succinates, tartrates, lactates, tosylates, benzenesulphonates, phosphates and acetates, and the addition salts thereof with a base such as sodium hydroxide, potassium hydroxide, ammonia, amines and alkanolamines.

The at least one oxidizing composition can also be used in a method of bleaching keratin fibers, for example human keratin fibers such as the hair.

In some embodiments, the method of bleaching comprises applying, to the keratin fibers, a bleaching composition for example comprising hydrogen peroxide in an alkaline medium after extemporaneous mixing. In some embodiments, the method of bleaching also comprises rinsing the keratin fibers.

In some embodiments, the bleaching composition applied to the keratin fibers can be obtained by mixing at least one oxidizing composition with an aqueous or anhydrous composition for example containing at least one alkaline agent. The anhydrous composition can be pulverulent or in the form of paste and, in both cases, may for example contain at least one peroxidized salt, such as at least one persulphate. The anhydrous composition in the form of paste may additionally contain at least one inert organic liquid.

Also provided is a method for permanently deforming keratin fibers, for example human keratin fibers such as the hair, using at least one oxidizing composition described herein.

This method comprises applying at least one reducing composition to the keratin fibers to be treated, placing the keratin fibers under mechanical tension before, during, or after application of the at least one reducing composition, optionally rinsing the fibers, applying the at least one oxidizing composition described herein to the optionally rinsed fibers, and then optionally rinsing the fibers again.

This method comprises applying at least one reducing composition to the hair. Application may be carried out lock by lock or globally.

The at least one reducing composition comprises at least one reducing agent, which may for example be selected from thioglycolic acid, cysteine, cysteamine, glycerol thioglycolate, thiolactic acid, and the salts thereof of thiolactic and thioglycolic acids.

The hair may be placed under tension in a form corresponding to the desired final form for the hair (curls for example) via any device or method, for example mechanical, that is appropriate and is known per se for keeping the hair under tension, for example rollers, curlers, combs, and the like.

The hair can also be shaped without using external aids, such as with the fingers.

Before optionally rinsing, the hair on which the at least one reducing composition has been applied should, conventionally, be left for some minutes, generally for a period of time ranging from 5 minutes to one hour, such as from 10 to 30 minutes, to give the at least one reducing agent time to act on the hair. This waiting period may for example be carried out at a temperature ranging from 35° C. to 45° C., for example while also protecting the hair with a cap.

The optional rinsing may be accomplished by carefully rinsing the hair impregnated with the at least one reducing composition with an aqueous composition.

Then, the at least one oxidizing composition described herein may be applied to the hair thus rinsed to fix the new shape imposed on the hair.

As in the case of application of the at least one reducing composition, the hair to which the at least one oxidizing composition has been applied may then, conventionally, be left alone for a resting or waiting period, which may last for a period of some minutes, for example ranging from 3 to 30 minutes, such as from 5 to 15 minutes.

If the tension of the hair has been maintained by external means, the latter (rollers, curlers and the like) can be removed from the hair before or after the fixation stage.

Finally, the hair impregnated with the at least one oxidizing composition may optionally be rinsed carefully, generally with water.

Also provided is the use of at least one oxidizing composition described herein for treating keratin fibers, for example human keratin fibers such as the hair.

Also provided is the use of at least one oxidizing composition described herein for dyeing keratin fibers, for example human keratin fibers such as the hair.

Also provided is the use of at least one oxidizing composition described herein for bleaching keratin fibers, for example human keratin fibers such as the hair.

Also provided is the use of at least one oxidizing composition described herein for the permanent deformation of keratin fibers, for example human keratin fibers such as the hair.

Also provided is a method for making an oxidizing composition for treating keratin fibers comprising combining, in a cosmetically acceptable medium:
 at least one cationic polymer;
 at least one fatty amide;
 at least one anti-oxygen agent; and
 at least one oxidizing agent;
 wherein the pH of the composition ranges from 1.5 to 4.5; and
 wherein the ingredients can be added in any order.

The following examples illustrate the disclosure but are not in any way limiting.

EXAMPLES

The following compositions were prepared:

| Composition | A | B | C |
|---|---|---|---|
| Diethylenetriamine pentaacetic acid, pentasodium salt in 40% aqueous solution | 0.15 g | 0.15 g | 0.15 g |
| Hydrogen peroxide in solution at 50% (hydrogen peroxide 200 volumes) | 12 g | 24 g | 12 g |
| Sodium stannate | 0.04 g | 0.04 g | 0.04 g |
| Tetrasodium pyrophosphate, 10H$_2$O | 0.03 g | 0.03 g | 0.03 g |
| Tetramethyl hexamethylenediamine/dichloro-1,3-propylene polycondensate in aqueous solution sold under the name MEXOMERE PO by the company Chimex | 0.25 g | 0.25 g | 0.25 g |
| Poly-dimethyl-diallyl ammonium chloride in water at 40%, unstabilized, sold under the name MERQUAT 100 by the company Nalco | 0.50 g | 0.50 g | 0.50 g |
| Deionized water | 75.73 g | 75.73 g | 75.73 g |
| Vaseline oil | — | — | 25 g |
| Glycerol | 0.50 g | 0.50 g | 0.50 g |
| Stearyl alcohol 30/70 | 8 g | 8 g | 8 g |
| Ceteareth-33 | 1.40 g | 1.40 g | 3 g |
| Ethoxylated amide of colza acids (4 EO) protected PEG-4 rapeseedamide | 1.30 g | 1.30 g | 1.30 g |
| Vitamin E | 0.10 g | 0.10 g | 0.10 g |
| Phosphoric acid q.s. | pH 2 | pH 2 | pH 2 |

Compositions A, B, and C were stable, even after 2 months stored at 45° C.

Similar results were obtained when the 0.25 g of MEXOMERE PO and the 0.5 g of MERQUAT 100 were replaced with 0.75 g of MERQUAT 100 and of MEXOMERE PO.

What is claimed is:

1. A composition for treating keratin fibers comprising:
 at least two cationic polymers comprising Polyquaternium-6 and hexadimethrine chloride;
 at least one fatty amide;
 at least one anti-oxygen agent;
 at least one non-silicone oil selected from mineral, vegetable, animal, or synthetic oils;
 at least one oxidizing agent comprising hydrogen peroxide; and
 a solvent comprising water and optionally at least one non-aqueous solvent;
 wherein the pH of the composition ranges from 1.5 to 4.5;
 wherein the at least one non-silicone oil is present in an amount of at least 20% by weight, relative to the total weight of the composition;
 wherein the composition does not include a hair dye; and
 wherein the composition is an oxidizing composition.

2. A composition for treating keratin fibers comprising:
 at least two cationic polymers comprising Polyquaternium-6 and hexadimethrine chloride;
 at least one fatty amide;
 at least one anti-oxygen agent selected from vitamin E, ethers thereof, or esters thereof;
 at least one non-silicone oil selected from mineral, vegetable, animal, or synthetic oils;
 at least one oxidizing agent comprising hydrogen peroxide; and
 a solvent comprising water and optionally at least one non-aqueous solvent;
 wherein the pH of the composition is alkaline,
 wherein the at least one non-silicone oil is present in an amount of at least 20% by weight, relative to the total weight of the composition;
 wherein the composition does not include a hair dye; and
 wherein the composition is an oxidizing composition.

3. The composition according to claim 1, wherein the at least one fatty amide is selected from those of formula (I):

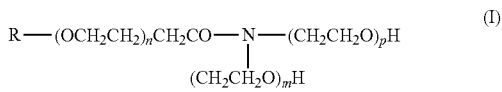

$$R-(OCH_2CH_2)_nCH_2CO-N(CH_2CH_2O)_mH-(CH_2CH_2O)_pH \quad (I)$$

wherein:
 R is a saturated or unsaturated, linear or branched $C_8$-$C_{30}$ alkyl radical, optionally substituted with at least one radical selected from an $OR_5$ radical, a $NR_6R_7$ radical, a carboxyl radical, a sulphonic radical, a carboxamido radical $CONR_6R_7$, a sulphonamido radical $SO_2NR_6R_7$, a heteroaryl, and an aryl radical optionally substituted with at least one entity selected from ($C_1$-$C_4$)alkyl, hydroxy, $C_1$-$C_2$ alkoxy, amino, and (di)alkyl($C_1$-$C_2$)amino groups;
 $R_5$, $R_6$ and $R_7$, which may be identical or different, represent:
  a hydrogen atom;
  a linear or branched $C_1$-$C_4$ alkyl radical, optionally substituted with at least one radical selected from a hydroxy, a $C_1$-$C_2$ alkoxy, a carboxamido $CONR_8R_9$, a sulphonyl $SO_2R_8$, and an aryl radical optionally substituted with a (C$_1$-C$_4$)alkyl, hydroxy, C$_1$-C$_2$ alkoxy, amino, or (di)alkyl(C$_1$-C$_2$) amino radical; or an aryl radical optionally substituted with a (C$_1$-C$_4$) alkyl, hydroxy, C$_1$-C$_2$ alkoxy, amino, or (di)alkyl (C$_1$-C$_2$)amino radical;

R$_6$ and R$_7$, which may be identical or different, can also represent a carboxamido radical CONR$_8$R$_9$ or a sulphonyl radical SO$_2$R$_8$, R$_8$ and R$_9$, which may be identical or different, represent a hydrogen atom or a linear or branched C$_1$-C$_4$ alkyl radical optionally substituted with at least one hydroxyl or C$_1$-C$_2$ alkoxy radical; and n, m and p, which may be identical or different, are integers ranging from 0 to 10, wherein m+p≥1.

4. The composition according to claim 3, wherein R is selected from a C$_{10}$-C$_{18}$ alkyl radical, n is an integer ranging from 0 to 5, m is an integer ranging from 0 to 1, and p is an integer ranging from 1 to 5.

5. The composition according to claim 3, wherein n is 0.

6. The composition according to claim 1, wherein the at least one fatty amide comprises an ethoxylated amide of colza acids.

7. The composition according to claim 1, wherein the at least one anti-oxygen agent is selected from vitamin E and the ethers and esters thereof.

8. The composition according to claim 1, wherein the composition further comprises at least one hydrogen peroxide stabilizer present in an amount ranging from about 0.0001% to about 5% by weight, relative to the total weight of the composition.

9. The composition of claim 8, wherein the at least one hydrogen peroxide stabilizer comprises a combination of at least one pyrophosphate and at least one stannate.

10. The composition of claim 1, wherein in the composition:
the at least one fatty amide is selected from PEG-4 rapeseedamide;
the at least one anti-oxygen agent is selected from vitamin E, ethers thereof, or esters thereof;
the at least one non-silicone oil is selected from mineral oil; and
the composition further comprises at least one hydrogen peroxide stabilizer chosen from pyrophosphates.

11. A composition comprising:
at least two cationic polymers comprising Polyquaternium-6 and hexadimethrine chloride;
at least one fatty amide;
at least one anti-oxygen agent;
at least one non-silicone oil selected from mineral, vegetable, animal, or synthetic oils;
at least one oxidizing agent comprising hydrogen peroxide;
at least one hydrogen peroxide stabilizer in an amount ranging from about 0.0001% to about 5% by weight, relative to the total weight of the composition; and
a solvent comprising water and optionally at least one non-aqueous solvent;
wherein the pH of the composition ranges from 1.5 to 4.5;
wherein the at least one non-silicone oil is present in an amount of at least 20% by weight, relative to the total weight of the composition;
wherein the composition does not include a hair dye; and
wherein the composition is an oxidizing composition.

12. The composition according to claim 8, wherein the at least one hydrogen peroxide stabilizer comprises at least one pyrophosphate or at least one stannate.

13. The composition according to claim 1, wherein the at least one fatty amide is present in an amount ranging from 0.5% to 5% by weight, relative to the total weight of the composition.

14. The composition according to claim 2, wherein the composition further comprises at least one hydrogen peroxide stabilizer comprising pyrophosphates and/or stannates.

15. The composition according to claim 2, wherein the at least one fatty amide is present in an amount ranging from 0.5% to 5% by weight, relative to the total weight of the composition.

16. A composition for treating keratin fibers comprising:
from 0.01% to 0.75% of at least two cationic polymers comprising Polyquaternium-6 and hexadimethrine chloride;
from 0.1% to 1.3% of at least one fatty amide comprising PEG-4 rapeseedamide;
at least one anti-oxygen agent comprising Vitamin E;
from 20% to 50% of at least one non-silicone oil comprising mineral oil;
from 1% to 12% of hydrogen peroxide; and
a solvent comprising water and optionally at least one non-aqueous solvent;
wherein all of the percentages are based on the total weight of the composition;
wherein the pH of the composition ranges from 1.5 to 4.5;
wherein the composition does not include a hair dye; and
wherein the composition is an oxidizing composition.

* * * * *